United States Patent [19]

Knepper et al.

[11] 4,094,898

[45] June 13, 1978

[54] PROCESS FOR THE PREPARATION OF SODIUM METHALLYL SULFONATE

[75] Inventors: Wilhelm Knepper; Dieter Jüergen Mueller, both of Marl, Germany

[73] Assignee: Chemische Werke Huels Aktiengesellschaft, Marl, Germany

[21] Appl. No.: 774,567

[22] Filed: Mar. 4, 1977

[30] Foreign Application Priority Data

Mar. 11, 1976 Germany .............................. 2610092

[51] Int. Cl.² .......................................... C07C 143/16
[52] U.S. Cl. ................................................. 260/513 B
[58] Field of Search ..................................... 260/513 B

[56] References Cited

U.S. PATENT DOCUMENTS

| 3,453,320 | 7/1969 | Robeson | 260/513 B |
| 3,755,430 | 8/1973 | Lorenz et al. | 260/513 B |

Primary Examiner—Nicky Chan

Attorney, Agent, or Firm—Millen & White

[57] ABSTRACT

Reaction of methallyl chloride (MAC) containing isocrotyl chloride (ICC) with aqueous sodium sulfite solution in an emulsion at 30°–80° C. and pH 7–11, maintained constant during the reaction by metered addition of sodium hydroxide solution is done in a two-step process, in the first step of which a mixture enriched in ICC and depleted in MAC from a preceding reaction batch and/or the second reaction step as excess organic residual phase, is reacted with an excess of concentrated sulfite solution until the MAC has been practically completely consumed; and, in the second step of which the reaction solution remaining after separating the unreacted ICC by distillation is reacted with a technical MAC/ICC mixture containing an excess of MAC until sulfite has been practically completely consumed. Thereafter, the excess organic residual phase is recycled to the first step after distillative separation. The MAC is preferably added in 10–40% excess in the second step.

10 Claims, No Drawings

PROCESS FOR THE PREPARATION OF SODIUM METHALLYL SULFONATE

BACKGROUND OF THE INVENTION

This invention relates to a process for the preparation of sodium methallyl sulfonate (MAS) from technical methallyl chloride (MAC) containing isocrotyl chloride (ICC) by a two-step reaction with aqueous sodium sulfite solution in an emulsion at temperatures of between 30° and 80° C.

Sodium methallyl sulfonate is an important monomer for copolymerization with other unsaturated monomers, particularly with acrylonitrile.

Commercial production of sodium methallyl sulfonate is carried out by reacting methallyl chloride with an aqueous solution of sodium sulfite at temperatures of 30°–70° C. The following equation represents the reaction:

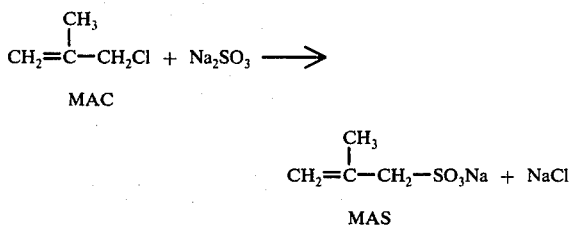

This reaction is generally done using an excess of methallyl chloride. Conversion to the sulfonate reaches as high as about 99.3%, when pure methallyl chloride is used (Russian Pat. No. 438,647).

Methallyl chloride is customarily made by the chlorination of isobutene and MAC is obtained as a mixture containing considerable amounts of isomeric isocrotyl chloride (ICC) and more highly chlorinated by-products. Although more highly chlorinated by-products can be separated relatively easily by fractional distillation, separation of ICC from MAC by further fractionation is very expensive and pure MAC is expensive. In commercial procedures, isomeric mixtures of about 80-95% by weight of MAC and 5-20% by weight of ICC are obtained without excessive expenditures. Use of technical MAC/ICC mixtures for MAS production would therefore be advantageous, owing to the low cost of the mixture.

Reaction of MAC, in a mixture containing ICC, with $Na_2SO_3$ is retarded by the presence of ICC, which does not react. When a technical mixture of 90% MAC and 10% ICC with a 1-2% excess of MAC with respect to $Na_2SO_3$ is used, reaction time is prolonged approximately four-fold, compared to the reaction time of pure MAC. Retardation of the reaction can essentially be prevented by using a larger excess of MAC, for example, a 20% excess. However, when a 20% excess of MAC is used, mixtures of 60% MAC and 40% ICC are obtained after the reaction. This product is unsuitable for conventional methods of making MAS because the reaction rate is retarded by ICC. Attempted separation of the mixture by distillation to attain enrichment with respect to MAC is very expensive, because the separation is difficult and there is a considerable loss in yield of MAC. Consequently, use of technical MAC in conventional processes becomes increasingly less economical as the ICC content of the technical MAC/ICC mixture increases. The ICC in the reaction mixture is also unusable, because separating this mixture by distillation to enrich ICC content is also uneconomical.

Thus, there is a continuing need for developing an economical process for preparing MAS from technical MAC/ICC mixtures and sodium sulfite, with high conversions of MAC and $Na_2SO_3$ and short reaction times.

SUMMARY OF THE INVENTION

This invention relates, in a process for the preparation of an aqueous solution of sodium methallyl sulfonate by the reaction of methallyl chloride and aqueous sodium sulfite solutions in an emulsion, to the improvement which comprises employing methallyl chloride containing isocrotyl chloride; maintaining the pH of the reaction mixture at a constant value of from 7-11 during the reaction by metered addition thereto of sodium hydroxide solution; and conducting the reaction in two stages in a cyclical process wherein in the first of the two stages, excess sodium sulfite is employed and the reaction is continued until the methallyl chloride therein is substantially entirely consumed and the resulting reaction product is fractionated by distillation to remove the isocrotyl chloride therefrom and leave as the residue an aqueous solution of sodium methallyl sulfonate and unreacted sodium sulfite; and wherein, in the second of the two stages, the thus-obtained aqueous solution of sodium methallyl sulfonate and unreacted sodium sulfite is reacted with excess technical methallyl chloride containing isocrotyl chloride, the reaction is continued until the sulfite therein has been substantially entirely consumed and the thus-obtained reaction product is fractionated by distillation to give as the distillate a mixture of methallyl chloride and isocrotyl chloride, which is recycled to the first of the two stages, and as the residue, an aqueous solution of sodium methallyl sulfonate.

DETAILED DESCRIPTION

The emulsion in which the reaction is carried out is produced mechanically by agitation, preferably without addition of an emulsifier. However, an emulsifier can be added to stabilize the emulsion. The reaction is done at temperatures of 30°–80° C., preferably at 65°–66° C. Above 66° C., i.e., the boiling temperature of a $MAC/H_2O$ mixture, the reaction is done under pressure. The heat of reaction is preferably removed by a reflux condenser unit.

The reaction is done at a pH of 7-11, preferably 9-10 pH 9-10 is optimum for a maximum rate of MAS formation and a minimum rate of MAC hydrolysis. The drop in pH caused by hydrolysis of MAC is compensated for by adding aqueous sodium hydroxide solution in metered amounts to maintain a preselected pH.

The process of this invention is conducted as follows. In the first step of the reaction, an aqueous, preferably saturated solution of $Na_2SO_3$ is combined with intensive agitation, preferably at temperatures of 35°–66° C., with a mixture of isomers depleted of MAC and enriched in ICC. This mixture is either obtained from a preceding process batch and/or from the second step after distillation of excess organic phase.

The composition and amount of the isomeric mixture depend on the MAC/ICC mixture utilized in the second step and the excess employed in this step. For example, if a technical mixture of isomers of about 90% MAC and about 10% ICC is utilized in the second step in an approximately 20% excess, an excess isomeric mixture of about 60% MAC and about 40% ICC is obtained after the reaction of the second step. This is utilized in the first step.

Any mixture of MAC/ICC can be used in the practice of this invention, preferably containing up to 40% ICC.

The solubility of $Na_2SO_3$ in water is a maximum of 28% by weight at 33.4° C. With rising temperature, solubility decreases, for example, to 24% by weight at 66° C. To obtain maximum yields of MAS, it is advantageous to use a 28% by weight $Na_2SO_3$ solution at 33.4° C. and/or a 27% by weight $Na_2SO_3$ solution at temperatures of 32°-40° C., preferably 40° C., or a 26% by weight $Na_2SO_3$ solution at temperatures of 30°-48° C., preferably 48° C., and to raise the reaction temperature gradually as the reaction proceeds so that no precipitation occurs. In raising the reaction temperature from 45° to 65° C., a time of 20-30 minutes is sufficient. More concentrated solutions of $Na_2SO_3$ are advantageously used when the MAS solution is to be worked up by evaporation.

The first reaction step is terminated when the MAC is practially completely converted to MAS, as is the case after about 60-70 minutes. Practically complete conversion of MAC means that less than about 0.1% of MAC remains unconverted. Thereafter, unreacted ICC is removed by distillation within a few minutes after reflux is terminated. Optionally the temperature is raised to a minor extent. After drying, ICC of 99.9% purity is thus obtained. Complete separation of ICC from the aqueous reaction solution is actually unnecessary, because an organic ICC-containing phase is recycled in the second step. Separation of ICC by distillation becomes more complete as the sump temperature is elevated.

After removing the bulk of the ICC, an aqueous reaction solution containing essentially $Na_2SO_3$, MAS, and NaCl, with a minor amount of ICC dissolved therein, is obtained.

In the second reaction step, the reaction solution, optionally cooled to $\leq$ 65° C., is combined with a technical isomeric mixture of, for example, 85-95% MAC and 5-15% ICI with a 20% excess of MAC, based on residual sulfite content in the reaction solution. The solution is made to react as in the first step with agitation and heating under reflux at the boiling point, preferably at pH 9-10. The drop in pH value caused by MAC hydrolysis is compensated for by adding aqueous NaOH in metered amounts, so that the optimum pH range of about 9-10 is maintained during the entire reaction period.

At the end of the second step, the content of $Na_2SO_3$ is no higher than 0.1%, preferably no higher than 0.05%.

Thereafter, excess organic phase, depleted of MAC and enriched in ICC, is separated by distillation by stopping cooling under reflux. Since the reaction solution must be evaporated in order to obtain pure MAS, the residual organic components dissolved therein are recovered quantitatively in the condensed vapor due to the increase in temperature required for concentration. The vapor can suitably be recycled for producing aqueous sulfite solution and thus prevent contamination of wastewater by chlorinated hydrocarbons.

The concentrated aqueous solution, which contains essentially MAS and NaCl is worked up by conventional methods, for example, by evaporation and fractional crystallization, to isolate the MAS.

The process of this invention makes it possible to use a technically readily accessible isomeric mixture of MAC and ICC, and permits almost quantitative conversion of MAC and $Na_2SO_3$ to MAS. During the distillative separation of the unreactable ICC after the first step, ICC of about 99.9% purity is obtained as a by-product after drying. The total reaction time, including separation of pure ICC, is within the range of conventional procedures, at most 3.5 hours. Due to the short reaction times and the pH maintained constant, loss of MAC by hydrolysis is likewise very low, amounting to less than 1%.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever. In the following examples, all temperatures are set forth uncorrected in degrees Celsius; unless otherwise indicated, all parts and percentages are by weight.

EXAMPLE 1

An agitator-equipped apparatus with provision for reflux condensation, equipped with temperature control, thermostat, pH meter, and a device for automatically maintaining pH constant by metered feeding of sodium hydroxide solution is maintained at a temperature of about 65° C. and chared with 2,604 g. of 24.0% by weight $Na_2SO_3$ solution containing 625 g. of $Na_2SO_3$ at about 65° C. This solution has a pH of 9.5. With intensive agitation, 125 g. of a mixture of 60% MAC and 40% ICC is added thereto. The pH is maintained constant by metered addition of 1N sodium hydroxide solution. After a reaction time of 70 minutes, the MAC is practically completely converted (>99,9%). The unreacted organic phase is removed by distillation at 66°-70° C. and dried. According to gas chromatography analysis, this phase is ICC of 99.9% purity.

The progress of the reaction can be followed by samnple removal and determination of sulfite in the aqueous phase and of the composition of the organic phase.

The aqueous phase, having a residual content of 19.4% by weight of $Na_2SO_3$, remaining after separation of ICC is cooled to 65° C. and combined in the second reaction step with 498.6 g. of a technical mixture of 90% MAC and 10% ICC (20% excess of MAC, based on sulfite present). The temperature is maintained at 65°-66° C. The pH of 9.5 is kept constant by metered addition of sodium hydroxide solution. After a total of 190 minutes in the first and second steps, the reaction is practically finished and the final concentration of $Na_2SO_3$ is 0.03%. The organic phase is removed by distillation. Yield: 125 g. of a mixture of 60% MAC and 40% ICC. This mixture is reused in the first reaction step. The aqueous phase contains 25.3% by weight of MAS. Hydrolyzed MAC proportion is, after the first reaction step, 0.1% and after the second reaction step, 0.7%, based on total MAC employed.

EXAMPLE 2

The agitator apparatus used in Example 1 is heated to a temperature of 45° C. and charged with 2,404 g. of a 26% $Na_2SO_3$ solution, warmed to 45° C., containing 625 g. of $Na_2SO_3$. With intensive agitation, 125 g. of a mixture of 60% MAC and 40% ICC is added thereto. The reaction mixture is raised within 20 minutes to a temperature of 65°-66° C. and the pH of 9.5 is kept constant as described in Example 1. Further reaction in the first and second reaction steps takes place at 65°–66° C. as in Example 1. After distilling the excess organic phase, which phase is recycled to the first step, an aqueous solution containing 27.1% of MAS is obtained. The amount of MAC hydrolyzed in both steps is a total of 0.85%.

COMPARATIVE EXAMPLE 3

In an experiment otherwise as in Example 1, the pH value of 9.5 is not kept constant. During the first reaction step, the pH drops to 9.1 and during the second reaction step, to pH 3. The reaction practically stops after about 300 minutes, at a sulfite concentration of about 0.09%. The thus-obtained MAS concentration is 25.2% and the amount of hydrolyzed MAC is more than 1%.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. In a process for the preparation of an aqueous solution of sodium methallyl sulfonate by the reaction of methallyl chloride and aqueous sodium sulfite solution in an emulsion, the improvement which comprises employing technical methallyl chloride containing isocrotyl chloride; maintaining the pH of the reaction mixture at a constant value of from 7-11 during the reaction by metered addition thereto of sodium hydroxide solution; and conducting the reaction in two stages in a cyclical process wherein, in the first of the two stages, excess sodium sulfite is employed and the reaction is continued until the methallyl chloride therein is substantially entirely consumed and the resulting reaction product is fractionated by distillation to remove the isocrotyl chloride therefrom and leave as the residue an aqueous solution of sodium methallyl sulfonate and unreacted sodium sulfite; and wherein, in the second of the two stages, the thus-obtained aqueous solution of sodium methallyl sulfonate and unreacted sodium sulfite is reacted with excess technical methallyl chloride containing isocrotyl chloride, the reaction is continued until the sulfite therein has been substantially entirely consumed and the thus-obtained reaction product is fractionated by distillation to give as the distillate a mixture of methallyl chloride and isocrotyl chloride, which is recycled to the first of the two stages, and as the residue, an aqueous solution of sodium methallyl sulfonate.

2. The process of claim 1, wherein a 10–40% excess of methallyl chloride is used in the second reaction stage.

3. The process of claim 1, wherein the reaction in the first and second stages is conducted at pH 9–10.

4. The process of claim 2, wherein the reaction in the first and second stages is conducted at pH 9–10.

5. The process of claim 1, wherein the temperature of each of said first and said second stages is 30°–80° C.

6. The process of claim 1, wherein the temperature of each of said first and second stages is 65°–66° C.

7. The process of claim 1, wherein the mixture used in the first stage is 60% methallyl chloride and 40% of isocrotyl chloride.

8. The process of claim 1, wherein the technical methallyl chloride used in said second stage is 85–95% of methallyl chloride and 5–15% of isocrotyl chloride, in an excess of 20% with respect to unreacted sodium sulfite in the residual aqueous solution from said first stage.

9. The process of claim 1, wherein the temperature in the first stage is raised from 45° to 65° C. over 20 to 30 minutes.

10. The process of claim 1, wherein
   (a) the reaction in each of said first and second stages is conducted at pH 9–10;
   (b) the temperature of each of said first and second stages is 65°–66° C.;
   (c) the mixture used in the first stage is 60% methallyl chloride and 40% of isocrotyl chloride; and
   (d) the technical methallyl chloride used in said second stage is 90% of methallyl chloride and 10% of isocrotyl chloride in an excess of 20% of methallyl chloride with respect to unreacted sodium sulfite in the residual aqueous solution from said first stage.

* * * * *